United States Patent [19]

Peck

[11] Patent Number: 5,588,452

[45] Date of Patent: Dec. 31, 1996

[54] TOOTH CLEANSING AND FLOSSING IMPLEMENT AND METHOD

[76] Inventor: Granger Peck, 6 Legend La., Sandy, Utah 84115

[21] Appl. No.: 438,258

[22] Filed: May 10, 1995

[51] Int. Cl.$^6$ .................................................. A61C 15/00
[52] U.S. Cl. .................................... 132/321; 132/329
[58] Field of Search ............................ 132/321, 329

[56] References Cited

U.S. PATENT DOCUMENTS

| | | | |
|---|---|---|---|
| 725,081 | 4/1903 | Hills | 132/329 |
| 3,511,249 | 5/1970 | Baitz | 132/329 |
| 3,590,814 | 7/1971 | Bennett | 132/321 |
| 3,779,256 | 12/1973 | Maloney et al. | 132/329 |
| 4,326,547 | 4/1982 | Verplank | 132/321 |
| 4,450,849 | 5/1984 | Cerceo et al. | 132/321 |
| 4,836,226 | 6/1989 | Wolak | 132/321 |
| 4,986,288 | 1/1991 | Kent et al. | 132/321 |
| 4,998,978 | 4/1991 | Varum | 132/321 |

*Primary Examiner*—Gene Mancene
*Assistant Examiner*—Pedro Philogene
*Attorney, Agent, or Firm*—Thorpe North & Western

[57] ABSTRACT

A combination toothpick and flossing device includes an elongate, generally flat strip of plastic having at least partially roughened surfaces. The strip is longitudinally stiff and laterally flexible and has dimensions which enable insertion thereof in gaps between adjacent teeth of a person. The plastic may be any polymer material which provides the characteristics of longitudinal stiffness and lateral flexibility such as polyester or nylon.

13 Claims, 1 Drawing Sheet

TOOTH CLEANSING AND FLOSSING IMPLEMENT AND METHOD

BACKGROUND OF THE INVENTION

The invention relates to a device and method for both cleaning, in the manner of a toothpick, and flossing teeth.

The use of toothpicks to clean teeth, typically after meals, has been practiced for many decades. Of more recent adoption but still long used is dental floss to perform what is termed "flossing" of teeth.

Toothpicks are most commonly made of wood and are formed into elongate cylindrical shafts with pointed ends or flattened shafts with at least one pointed end. To clean, the pointed ends are inserted between teeth and then manipulated in an attempt to remove whatever particles or matter may be caught between the teeth. The problem with wooden toothpicks, of course, is that they tend to splinter and therefore weaken easily, becoming useless for the purpose of cleaning teeth. Also, splinters may come off the toothpick in the mouth and ingested, which is unsafe. Further, wooden toothpicks are typically only useable one time and then must be discarded. Finally, it is difficult to insert the conventional wooden toothpick any significant distance between the teeth in an attempt to perform a flossing operation, and even if this were possible, the smooth sides of the toothpick would inhibit the effectiveness of any such flossing attempts.

Dental floss comprises long pieces of thread typically made of nylon, and either waxed or unwaxed, for drawing between teeth to remove food particles and prevent buildup of plaque. The floss must be small enough in diameter to fit between the teeth but also fairly strong so as not to break or fray. Flossing involves holding two ends of the floss and then manipulating it between each adjacent pairs of teeth. This can be quite difficult, especially for the larger molars at the back of the mouth. Also, once a length of floss has been used, it is typically so frayed and weakened that it cannot be used again.

SUMMARY OF THE INVENTION

It is an object of the invention to provide an implement and method for both cleaning and flossing teeth.

It is also an object of the invention to provide such an implement and method in which the implement employed may be reused without deterioration.

It is a further object of the invention to provide such an implement which is sturdy in construction and inexpensive to manufacture.

It is an additional object of the invention to provide such an implement which may be grasped by one hand to perform both cleaning and flossing.

The above and other objects are realized in a specific illustrative embodiment of a tooth cleansing and flossing implement comprising an elongate, slender shaft having generally planar upper and lower surfaces, and a thickness and width which allows insertion of the shaft between teeth. The upper and lower surfaces of the shaft are roughened to enhance the cleaning function and the shaft is constructed of a plastic material.

The tooth cleansing and flossing implement is used by grasping one end and inserting the other end between the teeth, and then moving the implement back and forth to both cleanse and floss the teeth.

In accordance with one aspect of the invention, the upper and lower surfaces of the shaft are formed with ridges in a cross-hatched pattern. Also the shaft is longitudinally stiff and laterally flexible to allow manipulation thereof in tight spaces.

BRIEF DESCRIPTION OF THE DRAWINGS

The above and other objects, features and advantages of the invention will become apparent from a consideration of the following detailed description presented in connection with the accompanying drawing which shows a tooth cleansing and flossing implement made in accordance with the principles of the present invention.

DETAILED DESCRIPTION

Figure 1A:
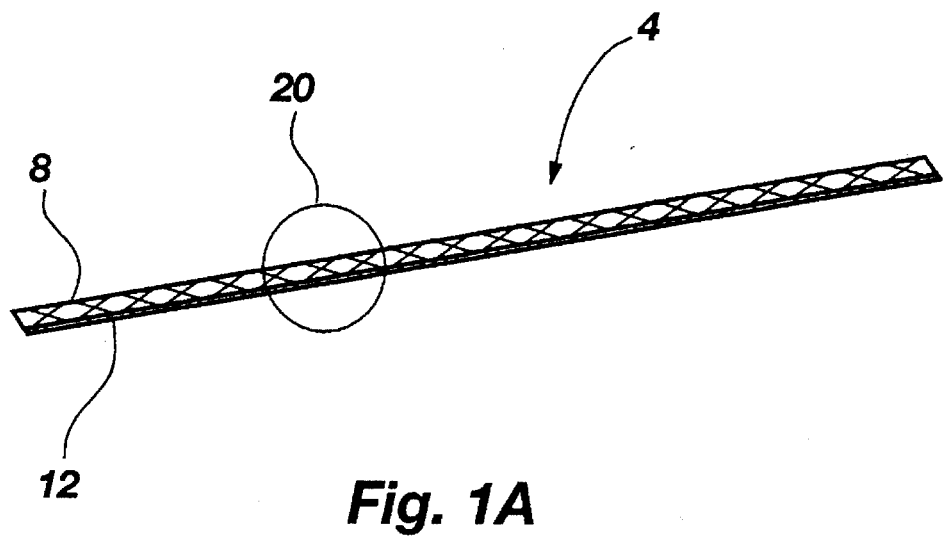
Figure 1B:
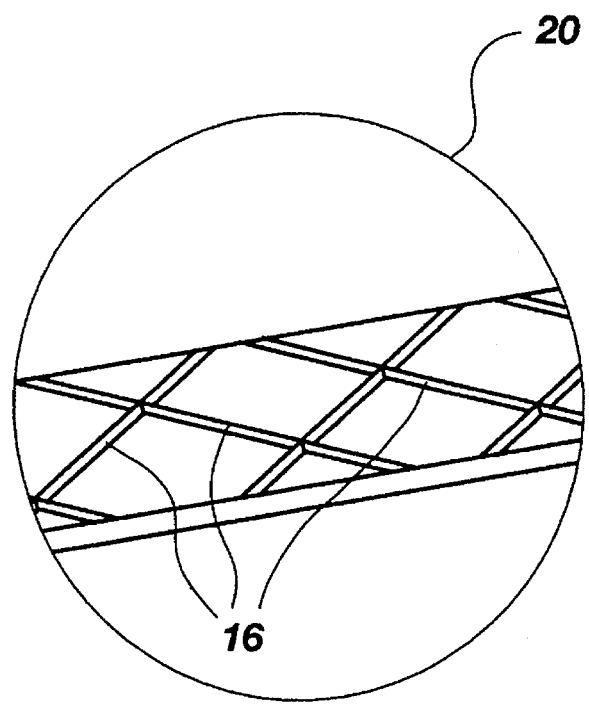

Referring to the drawing, there is shown a tooth cleansing and flossing implement made in accordance with the present invention to include an elongate, slender shaft 4 having generally planar upper (8) and lower (12) surfaces. The shaft is made of a polymer material such as polyester or nylon and is constructed to be generally longitudinally stiff and laterally flexible, and also resilient.

The upper and lower surfaces 8 and 12 of the shaft 4 are roughened or stippled so that when the shaft is inserted between adjacent teeth, the surfaces better aid in cleaning the teeth. The specific "roughening" shown in the embodiment in the drawing is of intersecting ridges 16 shown in the magnified section 20 of the shaft. The ridges, of course, could have various spacings and heights depending upon the desires of the user, and other protuberances such as nipples, parallel ridges, etc. could also be utilized.

Advantageously, the shaft 4 is from about 0.5 millimeters to 2.5 millimeters in width and from about 0.4 millimeters to 0.8 millimeters in thickness. The length may be selected to be whatever is most convenient for the users, for example, about 8 centimeters. With these dimensions, the shaft 4 may generally be inserted between most adjacent teeth of a person, at least at the location where the teeth emerge from the gums. Of course, some teeth are so closely positioned that the shaft could not be inserted between them and other mechanisms would have to be found.

Because the shaft 4 is longitudinally stiff and strong but laterally resilient, it is ideally suited for use both as a toothpick to dislodge materials caught between teeth and as a flossing implement to remove plaque between the teeth. Constructing the shaft 4 of a sturdy polymer material such as polyester or nylon results in a structure which may be used again and again without significant deterioration. That is, the implement need not be thrown away after each use.

The implement is used by simply grasping one end of the shaft and inserting the other end between the teeth of a person and then, for flossing, moving the strip back and forth in a reciprocating manner. If use of the implement as a toothpick is desired, then the implement would typically be grasped at about the midsection or even closer to the tip to be inserted between the teeth to thereby provide greater stiffness between the grasping location and the tip so that material could be more easily dislodged.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. A unitary tooth cleansing implement comprising an elongate, slender shaft having generally planar upper and lower surfaces, with a thickness of from about 0.4 millimeters to 0.8 millimeters and a width of from about 0.5 millimeters to 2.5 millimeters, the upper and lower surfaces being roughened, said shaft being constructed of polymer material and being longitudinally stiff and laterally flexible.

2. A tooth cleansing implement as in claim 1 wherein said shaft is constructed of polyester.

3. A tooth cleansing implement as in claim 1 wherein said shaft is constructed of nylon.

4. A tooth cleansing implement as in claim 1 wherein said upper and lower surfaces are formed with ridges.

5. A tooth cleansing implement as claim 4 wherein said ridges are formed in intersecting rows.

6. A tooth cleansing implement as in claim 4 wherein said ridges form cross-hatched patterns.

7. A tooth cleansing implement as in claim 1 wherein said upper and lower surfaces are formed with a plurality of protuberances.

8. A tooth cleansing implement as in claim 7 wherein said protuberances comprise ridges.

9. A tooth cleansing implement as in claim 1 wherein said shaft is longitudinally stiff and laterally flexible.

10. A tooth cleansing implement as in claim 9 wherein said shaft is laterally resilient.

11. A combination toothpick and flossing device comprising a unitary elongate generally flat strip of plastic having at least partially roughed surfaces, said strip being generally longitudinally stiff and laterally flexible, and having dimensions which enable insertion in gaps between adjacent teeth of a person.

12. The device of claim 11 wherein said strip has a width of from about 0.5 millimeter to 2.5 millimeters and a thickness of about 0.4 millimeters to 0.8 millimeters.

13. The device of claim 11 wherein the plastic is selected from the group consisting of polyester and nylon.

* * * * *